(12) United States Patent
Corma Canos et al.

(10) Patent No.: US 9,856,145 B2
(45) Date of Patent: Jan. 2, 2018

(54) MATERIAL ITQ-55, METHOD FOR PREPARATION AND USE

(71) Applicants: Avelino Corma Canos, Valencia (ES); Fernando Rey Garcia, Valencia (ES); Susana Valencia Valencia, Valencia (ES); Angel Cantin Sanz, Valencia (ES); Jose Luis Jordá Moret, Valencia (ES)

(72) Inventors: Avelino Corma Canos, Valencia (ES); Fernando Rey Garcia, Valencia (ES); Susana Valencia Valencia, Valencia (ES); Angel Cantin Sanz, Valencia (ES); Jose Luis Jordá Moret, Valencia (ES)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 412 days.

(21) Appl. No.: 14/744,169

(22) Filed: Jun. 19, 2015

(65) Prior Publication Data

US 2016/0009563 A1 Jan. 14, 2016

(51) Int. Cl.
*C01B 39/48* (2006.01)
*C01B 37/02* (2006.01)
(Continued)

(52) U.S. Cl.
CPC .............. *C01B 39/48* (2013.01); *B01D 53/02* (2013.01); *B01D 53/04* (2013.01);
(Continued)

(58) Field of Classification Search
CPC ......... C01B 37/02; C01B 39/06; C01B 39/08; C01B 39/12; C01B 39/48; B01J 20/18; B01J 29/70; B01J 29/86; B01J 29/89
See application file for complete search history.

(56) References Cited

U.S. PATENT DOCUMENTS

| 5,871,650 A | 2/1999 | Lai et al. |
| 6,734,129 B2 | 5/2004 | Lai et al. |

(Continued)

FOREIGN PATENT DOCUMENTS

| CA | 2306311 A1 | 10/2001 |
| WO | 2013156638 A1 | 10/2013 |
| WO | 2014122344 A1 | 8/2014 |

OTHER PUBLICATIONS

Jiang et al., "ITQ-54: a multi-dimensional extra-large pore zeolite with 20×14×12—ring channels", Chemical Science, Jan. 1, 2015, pp. 480-485, vol. 6, Iss. 1, Royal Society of Chemistry.
(Continued)

*Primary Examiner* — David M Brunsman
(74) *Attorney, Agent, or Firm* — Andrew T. Ward

(57) ABSTRACT

This invention refers to a microporous crystalline material of zeolitic nature that has, in its calcined state and in the absence of defects in its crystalline matrix manifested by the presence of silanols, the empirical formula $$x(M_{1/n}XO_2):yYO_2:gGeO_2:(1-g)SiO2$$

in which
M is selected between $H^+$, at least one inorganic cation of charge +n, and a mixture of both,
X is at least one chemical element of oxidation state +3,
Y is at least one chemical element with oxidation state +4 different from Si,
x takes a value between 0 and 0.2, both included,
y takes a value between 0 and 0.1, both included,
g takes a value between 0 and 0.5, both included
that has been denoted ITQ-55, a method for its preparation and its use.

25 Claims, 5 Drawing Sheets

(51) Int. Cl.

| | |
|---|---|
| *B01J 20/18* | (2006.01) |
| *B01J 29/70* | (2006.01) |
| *B01D 71/02* | (2006.01) |
| *B01D 53/04* | (2006.01) |
| *B01D 53/047* | (2006.01) |
| *C01B 3/50* | (2006.01) |
| *B01D 53/02* | (2006.01) |
| *B01D 53/22* | (2006.01) |
| *C01B 17/16* | (2006.01) |
| *C01B 21/04* | (2006.01) |
| *C01C 1/12* | (2006.01) |
| *B01J 20/30* | (2006.01) |
| *C07C 1/20* | (2006.01) |
| *C07C 1/32* | (2006.01) |
| *C07C 2/76* | (2006.01) |
| *C07C 29/00* | (2006.01) |
| *C07C 41/01* | (2006.01) |
| *C01B 39/06* | (2006.01) |
| *C01B 39/08* | (2006.01) |
| *C01B 37/00* | (2006.01) |
| *C01B 39/12* | (2006.01) |
| *B01J 29/89* | (2006.01) |
| *B01J 29/86* | (2006.01) |

(52) U.S. Cl.
CPC ....... *B01D 53/0407* (2013.01); *B01D 53/047* (2013.01); *B01D 53/0462* (2013.01); *B01D 53/228* (2013.01); *B01D 53/229* (2013.01); *B01D 71/028* (2013.01); *B01J 20/18* (2013.01); *B01J 20/3078* (2013.01); *B01J 29/70* (2013.01); *C01B 3/508* (2013.01); *C01B 17/167* (2013.01); *C01B 21/0466* (2013.01); *C01B 37/002* (2013.01); *C01B 37/007* (2013.01); *C01B 37/02* (2013.01); *C01B 39/06* (2013.01); *C01B 39/08* (2013.01); *C01B 39/12* (2013.01); *C01C 1/12* (2013.01); *C07C 1/20* (2013.01); *C07C 1/322* (2013.01); *C07C 2/76* (2013.01); *C07C 29/00* (2013.01); *C07C 41/01* (2013.01); *B01D 2253/108* (2013.01); *B01D 2256/10* (2013.01); *B01D 2256/12* (2013.01); *B01D 2256/16* (2013.01); *B01D 2256/18* (2013.01); *B01D 2256/20* (2013.01); *B01D 2256/22* (2013.01); *B01D 2256/24* (2013.01); *B01D 2256/245* (2013.01); *B01D 2256/26* (2013.01); *B01D 2257/302* (2013.01); *B01D 2257/304* (2013.01); *B01D 2257/40* (2013.01); *B01D 2257/404* (2013.01); *B01D 2257/406* (2013.01); *B01D 2257/50* (2013.01); *B01D 2257/504* (2013.01); *B01D 2257/70* (2013.01); *B01D 2257/702* (2013.01); *B01D 2257/7022* (2013.01); *B01D 2257/80* (2013.01); *B01J 29/86* (2013.01); *B01J 29/89* (2013.01); *C01B 2203/0405* (2013.01); *C01B 2210/0018* (2013.01); *C07C 2529/70* (2013.01); *C07C 2529/76* (2013.01); *C07C 2529/78* (2013.01); *Y02C 10/08* (2013.01)

(56) References Cited

U.S. PATENT DOCUMENTS

| | | | |
|---|---|---|---|
| 7,049,259 | B1 | 5/2006 | Deckman et al. |
| 7,094,275 | B2 | 8/2006 | Keefer et al. |
| 7,476,635 | B2 | 1/2009 | Chau et al. |
| 7,498,011 | B2 | 3/2009 | Cao et al. |
| 7,828,875 | B2 | 11/2010 | Li et al. |
| 7,959,720 | B2 | 6/2011 | Deckman et al. |
| 8,002,880 | B2 | 8/2011 | Carruthers |
| 8,067,327 | B2 | 11/2011 | Li et al. |
| 8,529,664 | B2 | 9/2013 | Deckman et al. |
| 8,603,432 | B2 | 12/2013 | Andersen et al. |
| 8,641,810 | B2 | 2/2014 | McAlister |
| 9,617,164 | B2 * | 4/2017 | Corcoran, Jr. ............ C07C 2/76 |
| 9,688,542 | B2 * | 6/2017 | Corcoran, Jr. ............ C07C 2/76 |
| 9,695,056 | B2 * | 7/2017 | Corcoran, Jr. ............ C07C 2/76 |
| 9,738,539 | B2 * | 8/2017 | Corcoran, Jr. ......... C01B 39/48 |
| 2006/0169142 | A1 | 8/2006 | Rode et al. |
| 2006/0189476 | A1 | 8/2006 | Deckman et al. |
| 2006/0252631 | A1 | 11/2006 | Deckman et al. |
| 2009/0111959 | A1 | 4/2009 | Cao et al. |
| 2014/0122344 | A1 * | 5/2014 | Foulds ............ G06Q 20/38215 705/67 |
| 2015/0011815 | A1 | 1/2015 | Ma et al. |
| 2015/0038756 | A1 * | 2/2015 | Corma Canos ......... C01B 39/48 585/640 |

OTHER PUBLICATIONS

International Search Report with Written Opinion from PCT/US2015/036584 dated Jun. 19, 2015.

International Search Report with Written Opinion from PCT/US2015/036601 dated Jun. 19, 2015.

International Search Report with Written Opinion from PCT/US2015/036647 dated Jun. 19, 2015.

International Search Report with Written Opinion from PCT/US2015/036636 dated Jun. 19, 2015.

Anderson et al., "The crystal structure of lithium hydrazinium flouroberyllate", Acta Crystallographica Section B, Structural Science B, Crystal Engineering and Materials, Nov. 1973, pp. 2625-2627, vol. 29, iss. 11, Wiley Online Library.

Meier, et al., "The Topology of Three-Dimensional 4-Connected Nets: Classification of Zeolite Framework Types Using Coordination Sequences", Journal of Solid State Chemistry, Mar. 1979, pp. 349-355, vol. 27, iss. 3, Science Direct.

Reyes et al.,"Frequency Modulation Methods for Diffusion and Adsorption Measurements in Porous Solids", Journal of Physical Chemistry B, Jan. 23, 1997, pp. 614-622, vol. 101, iss. 4, ACS Publications.

Koller et al., "Five-Coordinate Silicon in High-Silica Zeolites", Journal of American Chemical Society, Mar. 23, 1999, pp. 3368-3376, vol. 121, iss. 14, ACS Publications.

Sastre et al., "ZeoTsites: a code for topological and crystallographic tetrahedral sites analysis in zeolites and zeotypes", Microporous and Mesoporous Materials, Mar. 2001, pp. 27-40, vol. 43, iss. 1, ScienceDirect, Elsevier.

Tuel et al., "NMR Characterization and Rietveld Refinement of the Structure of Rehydrated AlPO 4-34", Journal of Physical Chemistry B, in J. Phys. Chem. B, May 26, 2000, pp. 5697-5705, vol. 104, iss. 24, ACS Publications.

Serre et al., "Hydrothermal synthesis, structure determination from powder data of a three-dimensional zirconium diphosphonate with an exceptionally high thermal stability: Zr(O3P—(CH2)—PO3) or MIL-57", Journal of Materials Chemistry, Jun. 12, 2002, pp. 2367-2369, vol. 12, The Royal Society of Chemistry.

Zheng, "Microporous and Photoluminescent Chalcogenide Zeolite Analogs"Science, Dec. 20, 2002, pp. 2366-2369, vol. 298, AAAS, HighWirePress.

Huang et al., "Ligand-Directed Strategy for Zeolite-Type Metal—Organic Frameworks: Zinc(II) Imidazolates with Unusual Zeolitic Topologies", Angewandte Chemie International Edition, Jan. 27, 2006, pp. 1557-1559, vol. 45, iss. 10, Wiley Online Library.

Broach et al., "Zeolites", Ulmann's Encyclopedia of Industrial Chemistry, pp. 1-35, 2012, Wiley-VCH Verlag GmbH & Co. KGaA, Weinheim.

Park et al., "Effects of cagge shape and size of 8-membered ring sieves on their deactivation in methanol-to-olefin (MTO) reactions", Applied Catalysis A: General, Jan. 17, 2008, pp. 36-44, vol. 339, Science Direct, Elsevier.

* cited by examiner

Framework Structure of ITQ-55 showing only the tetrahedral atoms. There is a single unit cell, whose edges are defined by the gray box.

MATERIAL ITQ-55, METHOD FOR PREPARATION AND USE

CLAIM OF FOREIGN PRIORITY

Pursuant to 35 U.S.C. 119(a), this application claims the benefit of Application No. P201430935 filed in Spain, reception office OEPM Madrid, on Jun. 20, 2014 which is incorporated by reference herein in its entirety.

CROSS-REFERENCE TO RELATED APPLICATIONS

This application is related to four other co-pending U.S. applications, filed on Jun. 19, 2015 as follows: Ser. Nos. 14/744,485; 14/744,334; 14/744,248; and 14/744,211. Each of these co-pending U.S. applications are hereby incorporated by reference herein in their entirety.

FIELD OF THE INVENTION

This invention belongs to the technical field of microporous crystalline materials of zeolitic nature, useful as adsorbents, catalysts or catalytic components, for transformation processes and in particular for the adsorption and separation of organic and inorganic compound in gas or liquid phase.

BACKGROUND OF THE INVENTION

Zeolites are a microporous crystalline material formed by a matrix of TO4 tetrahedrons that share all their vertices giving rise to a three-dimensional structure that contains channels and/or cavities of molecular dimensions. They are of variable composition, and T generally represents atoms with formal oxidation state +3 or +4, such as for example Si, Ge, Ti, Al, B, or Ga. When some of the T atoms have an oxidation state less than +4, the crystalline matrix formed presents negative charges that are compensated by means of the presence in the channels or cavities of organic or inorganic cations. These channels and cavities may also contain organic molecules and $H_2O$, therefore, in a general manner, the chemical composition of the zeolites may be represented by means of the following empirical formula:

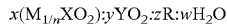

where M is one or several organic or inorganic cations of charge $+n$; X is one or several trivalent elements; Y is one or several tetravalent elements, generally Si; and R is one or several organic substances. Although by means of postsynthesis treatments the nature of M, X, Y and R and the values of x, y, z, and w may vary, the chemical composition of a zeolite (just as is synthesized or after its calcining) possesses a characteristic range for each zeolite and its method of preparation.

The crystalline structure of each zeolite, with a system of channels and specific cavities, gives rise to a characteristic diffraction pattern of X-rays, which allows one to differentiate them from each other.

Many zeolites have been synthesized in presence of an organic molecule that acts as a structure director agent. The organic molecules that act as structure director agents (SDA) generally contain nitrogen in their composition, and they can give rise to stable organic cations in the reaction medium.

The mobilization of the precursor species during the zeolites synthesis may be carried out in the presence of hydroxyl groups and basic medium that can be introduced as hydroxide of the same SDA, such as for example tetrapropylammonium hydroxide in the case of the zeolite ZSM-5.

The fluoride ions can also act as mobilizing agents in synthesis of zeolites, for example in the patent EP-TO-337479 the use of HF is described in $H_2O$ at low pH as a mobilizing agent of silica for the zeolite ZSM-5 synthesis.

SUMMARY OF THE INVENTION

This invention refers to a new microporous crystalline material of zeolitic nature, identified as "zeolite ITQ-55," its preparation method and its use.

ITQ-55 (INSTITUTO DE TECNOLOGÍA QUÍMICA number 55) is a new crystalline microporous material having a framework of tetrahedral atoms connected by bridging atoms, the tetrahedral atom framework being defined by the interconnections between the tetrahedrally coordinated atoms in its framework. ITQ-55 is stable to calcination in air, absorbs hydrocarbons, and is catalytically active for hydrocarbon conversion.

This material, both in its calcined form and synthesized without calcining has an X-ray diffraction pattern that is different from other well-known zeolitic material and, therefore, is characteristic of this material.

DETAILED DESCRIPTION OF THE EMBODIMENTS

Figure 1:
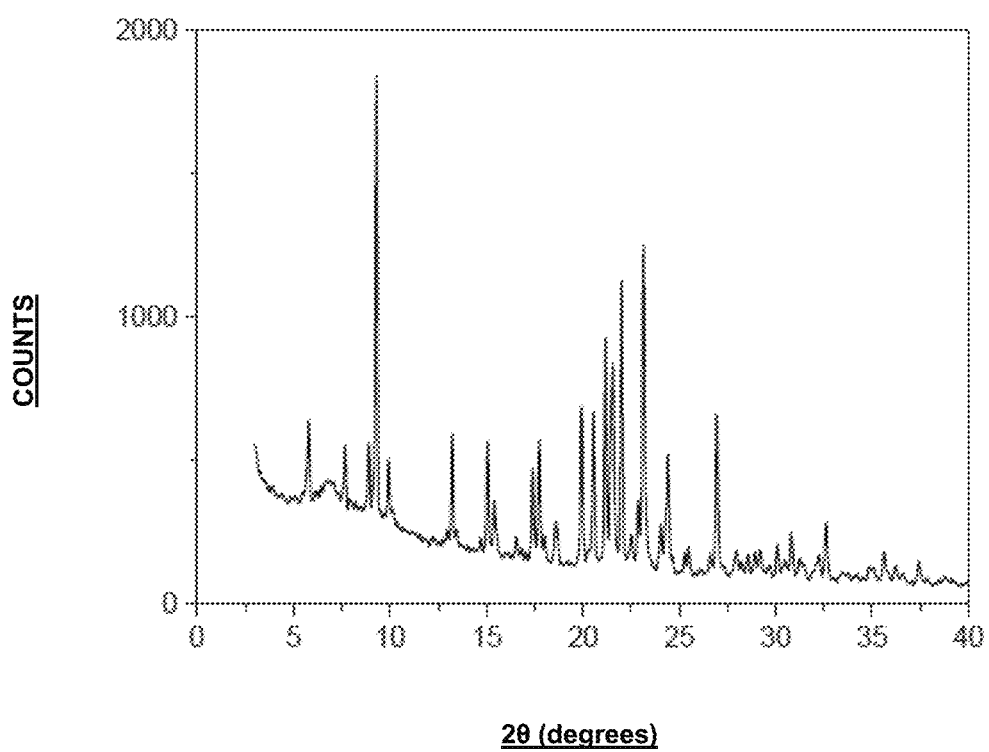
FIG. 1 represents the X-ray diffraction pattern of the most characteristic peaks of the purely siliceous ITQ-55 material, as is synthesized, obtained according to Example 2.

This invention refers in the first place to a microporous crystalline material of zeolitic nature that has, in calcined state and in absence of defects in its crystalline matrix manifested by the presence of silanols, the empirical formula

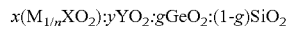

in which,

M is selected among H+, at least one inorganic cation of charge +n, and a mixture of both, preferably selected among H+, at least one inorganic cation of charge +n selected among alkaline, alkaline-earth metals and combinations thereof, and a mixture of both, X is at least one chemical element of oxidation state +3, selected preferably between Al, Ga, B, Fe, Cr and mixtures of the same.

Y is at least one chemical element with oxidation state +4 different from Si, selected preferably between Ti, Sn, Zr, V and mixtures of the same.

x takes a value between 0 and 0.2, both included, preferably less than 0.1.

y takes a value between 0 and 0.1, both included, preferably less than 0.05.

g takes a value between 0 and 0.5, both included, preferably less than 0.33.

and because the material, as it is synthesized, has an X-ray diffraction pattern with, at least, the angle values 2θ (degrees) and relative intensities ($I/I_0$) shown in the Table I, $I_0$ being the intensity of the highest peak to which is assigned a value of 100:

TABLE I

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where w is a relative weak intensity between 0 and 20%, m is an relative medium intensity between 20 and 40%, f is a relative strong intensity between 40 and 60%, and mf is a very strong relative intensity between 60 and 100%.

The microporous crystalline material of zeolitic nature according to the invention, after being calcined to eliminate the organic compounds occluded in its interior, possesses an X-ray diffraction pattern with, at least, the angle values 2θ(degrees) and relative intensities ($I/I_0$) indicated in the Table II:

TABLE II

| 2θ (degrees) ± 0.5 | Intensity ($I/I_0$) |
|---|---|
| 6.2 | w |
| 7.8 | w |
| 8.0 | w |
| 9.8 | mf |
| 10.0 | m |
| 10.3 | w |
| 12.3 | w |
| 13.4 | w |
| 13.7 | w |
| 15.0 | w |
| 15.2 | w |
| 16.8 | w |
| 18.1 | w |
| 20.1 | w |
| 21.3 | w |
| 23.5 | w |
| 23.9 | w |
| 26.8 | w | where w, m, f and mf have the previous meaning

According to a preferred embodiment of this invention the microporous crystalline material of zeoltic nature ITQ-55, has, in calcined state and in absence of defects in its crystalline matrix manifested by the presence of silanols, the empirical formula

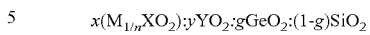

in which

M is selected among $H^+$, at least one inorganic cation of charge +n, preferably alkaline or alkaline earth, alkaline, alkaline-earth metals and combinations of the same, X is at least one chemical element of oxidation state +3, selected between Al, Ga, B, Fe, Cr and mixtures of the same, Y is at least one chemical element with oxidation state +4 different from Si, selected among Ti, Sn, V, Zr and mixtures of the same, x takes a value between 0 and 0.1, both included, y takes a value between 0 and 0.05, both included, g takes a value between 0 and 0.33, both included, and the material, as is synthesized, has an X-ray diffraction pattern with at least, the angle values 2θ (degrees) and relative intensities mentioned previously (Table I) and this material in calcined state has an X-ray diffraction pattern with, at least, the angle values 2θ (degrees) and relative intensities ($I/I_0$) mentioned previously (Table II).

According to a preferred embodiment of this invention the microporous crystalline material of zeolitic nature ITQ-55 is a pure silica material, that is to say that in the general formula indicated previously "x", "y" and "g" they take the value 0.

According to another preferred embodiment of this invention the microporous crystalline material of zeolitic nature ITQ-55 is a material that can have in the general formula previously indicated "x" equal to 0, "y" equal to 0 and "g" different from 0.

According to another preferred embodiment of this invention the microporous crystalline material of zeolitic nature ITQ-55 is a material in whose general formula:

X is selected between Al, Ga, B, Fe, Cr, and combinations of the same, y takes the value 0, and g takes the value 0.

Another preferred embodiment of this invention the microporous crystalline material of zeolitic nature ITQ-55 is a material, which can have in its general formula:

Y is selected between Ti, Zr, Sn, and combinations of the same, x takes the value 0, and g takes the value 0.

According to another preferred embodiment the microporous crystalline material of zeolitic nature ITQ-55 is a material in whose general formula:

X is Al, Ga, B, Fe, Cr, and combinations of the same,

Y is Ti, Zr, Sn, and combinations of the same and g take the value 0.

In one particular embodiment, the microporous crystalline material of zeolitic nature ITQ-55 is a material in whose general formula:

X is Al, Ga, B, Fe, Cr, and combinations of the same, y takes the value 0, and g takes a value different from 0 and less than 0.33.

Another particular embodiment describes the microporous crystalline material of zeolitic nature ITQ-55 in whose general formula:

Y is Ti, Zr, Sn, and combinations of the same, x takes the value 0, and g takes a value different from 0 and less than 0.33.

In another particular embodiment, the microporous crystalline material of zeolitic nature ITQ-55 is a material in whose general formula:

X is Al, Ga, B, Fe, Cr, and combinations of the same,
Y is Ti, Zr or Sn, and
g takes a value different from 0 and less than 0.33.

The X-ray diffraction patterns of the ITQ-55 material has been obtained by the powder method using a fixed divergence slit of ⅛° and using the Kα radiation of Cu. It should be kept in mind that the diffraction data listed for this zeolite sample ITQ-55 as single or unique lines, can be formed from multiple overlapping reflections that, under certain conditions, such as differences in crystallographic changes, may appear as resolved or partially resolved lines. Generally, the crystallographic changes may include small variations in the parameters of the unit cell and/or changes in the symmetry of the unit cell, without a change taking place in the structure. Thus, the positions, widths and relative intensities of the peaks depend in a certain measure on the chemical composition of the material, as well as of the degree of hydration and the crystal size.

In particular, when the matrix is composed exclusively by silicon oxide and has been synthesized in the presence of fluoride anions using the quaternary cation diammonium $N^2,N^2,N^2,N^5,N^5,N^5,3a,6a$-octamethylo-octahydropentalene-2,5-diammonium as structure director agent, the ITQ-55 zeolite as synthesized presents an X-ray diffraction pattern like the one that is shown in FIG. 1. This diagram is characterized by the angle values 2θ (degrees) and relative intensities ($I/I_0$) that are presented in Table III, where w, m, f and mf have the same meaning as in the Table I.

TABLE III

| 2θ (degrees) ± 0.5 | Intensity ($I/I_0$) |
|---|---|
| 5.78 | w |
| 7.68 | w |
| 8.91 | w |
| 9.31 | mf |
| 9.93 | w |
| 10.14 | w |
| 13.23 | m |
| 13.42 | w |
| 14.70 | w |
| 15.06 | m |
| 15.40 | w |
| 15.52 | w |
| 16.55 | w |
| 16.84 | w |
| 17.05 | w |
| 17.40 | m |
| 17.73 | m |
| 18.02 | w |
| 18.60 | w |
| 19.93 | m |
| 20.56 | m |
| 21.17 | f |
| 21.47 | m |
| 21.56 | f |
| 22.01 | f |
| 22.51 | w |
| 22.88 | w |
| 23.14 | mf |
| 24.05 | w |
| 24.42 | m |
| 24.62 | w |
| 25.28 | w |
| 25.49 | w |
| 26.61 | w |
| 26.95 | m |
| 27.95 | w |
| 28.24 | w |
| 28.59 | w |

TABLE III-continued

| 2θ (degrees) ± 0.5 | Intensity ($I/I_0$) |
|---|---|
| 28.93 | w |
| 29.21 | w |
| 29.68 | w |

Figure 2:
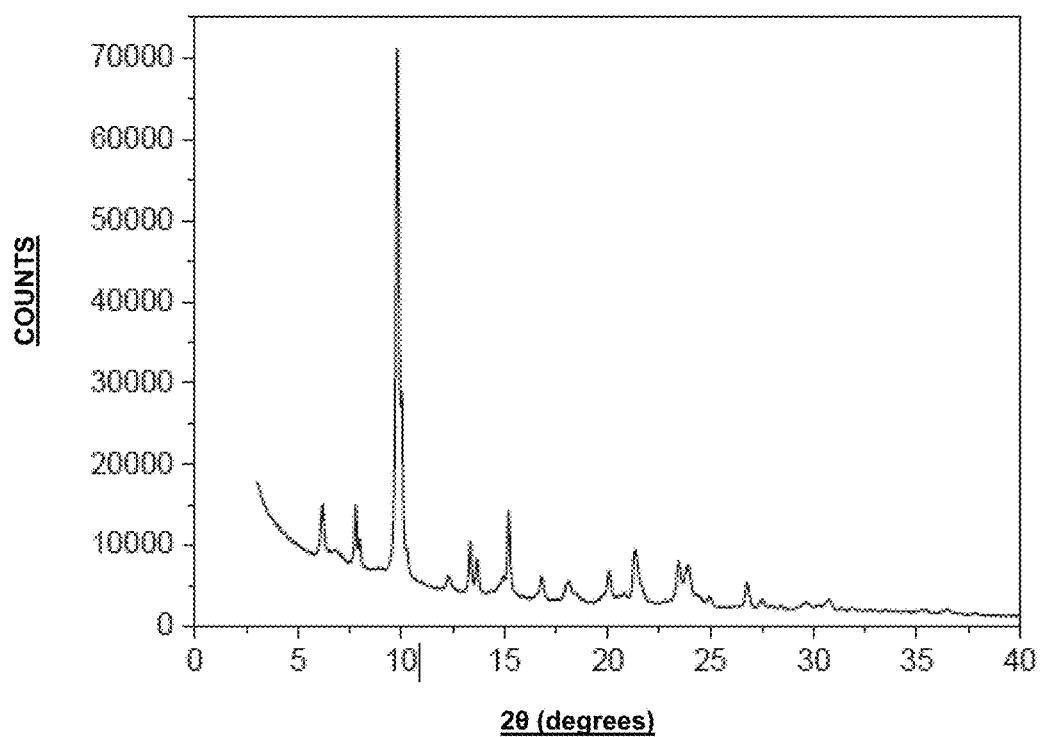
FIG. 2 represents the X-ray diffraction pattern of the most characteristic peaks of the material of the example 2 in calcined state.

The X-ray diffraction pattern of the previous sample of ITQ-55 after being calcined at 800° C. to eliminate the organic compounds occluded in its interior is shown in the FIG. 2. This diffractogram is characterized by the angle values 2θ (degrees) and relative intensities ($I/I_0$) that are shown in the Table IV, where w, m, f and mf have the same meanings as in Table I. The comparison of the diffractograms of X-rays corresponding to zeolite ITQ-55 as is synthesized and in calcined state show that the material is thermally stable.

TABLE IV

| 2θ (degrees) | Intensity ($I/I_0$) |
|---|---|
| 6.18 | w |
| 7.80 | w |
| 7.98 | w |
| 9.82 | mf |
| 10.02 | m |
| 10.29 | w |
| 12.31 | w |
| 13.35 | w |
| 13.68 | w |
| 14.98 | w |
| 15.22 | w |
| 15.52 | w |
| 16.82 | w |
| 18.09 | w |
| 18.43 | w |
| 20.06 | w |
| 20.81 | w |
| 21.34 | w |
| 21.67 | w |
| 23.45 | w |
| 23.92 | w |
| 24.39 | w |
| 24.99 | w |
| 26.80 | w |
| 27.48 | w |
| 27.91 | w |
| 28.43 | w |
| 29.61 | w |

As with any porous crystalline material, the structure of ITQ-55 can be defined not only by its X-ray diffraction pattern but by its framework structure, i.e., the interconnections between the tetrahedrally coordinated atoms in its framework. In particular, ITQ-55 has a framework of tetrahedral (T) atoms connected by bridging atoms, wherein the tetrahedral atom framework is defined by connecting the nearest tetrahedral (T) atoms in the manner given in Table V.

TABLE V

| ITQ-55 tetrahedral atom interconnections | |
|---|---|
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |

TABLE V-continued

ITQ-55 tetrahedral atom interconnections

| T atom | Connected to: |
|---|---|
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67 |

Tetrahedral atoms are those capable of having tetrahedral coordination, including one or more of, but not limiting, lithium, beryllium, boron, magnesium, aluminum, silicon, phosphorous, titanium, chromium, manganese, iron, cobalt, nickel, copper, zinc, zirconium, gallium, germanium, arsenic, indium, tin, and antimony.

The synthetic porous crystalline material of this invention, ITQ-55, is a crystalline phase which has a unique 1-dimensional channel system comprising 8-member rings of tetrahedrally coordinated atoms.

Figure 5:
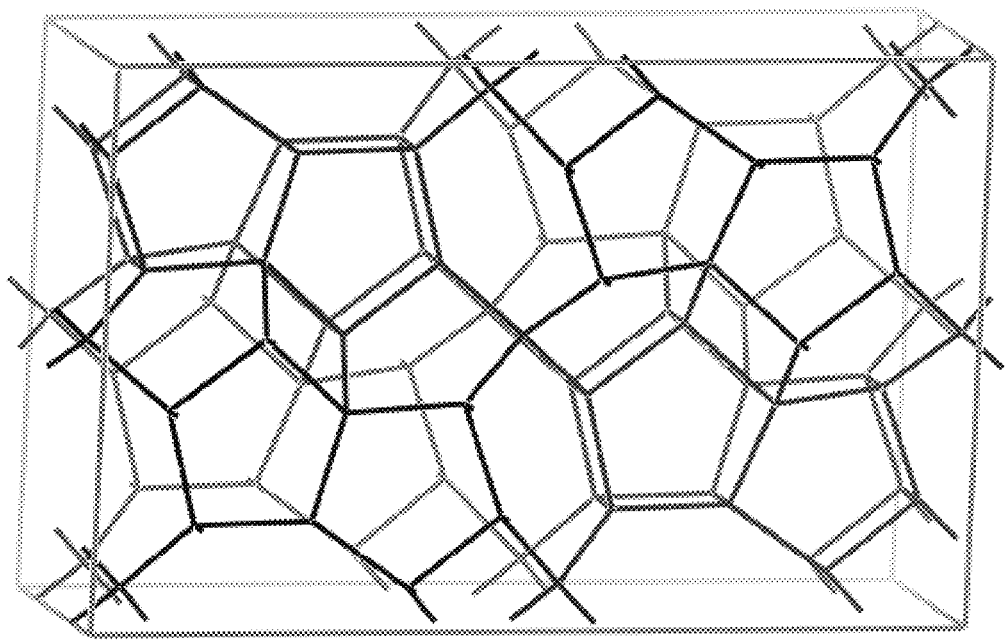
FIG. 5 represents the framework structure of ITQ-55 showing only the tetrahedral atoms.

In addition, to describing the structure of ITQ-55 by the interconnections of the tetrahedral atoms as in Table V above, it may be defined by its unit cell, which is the smallest repeating unit containing all the structural elements of the material. The pore structure of ITQ-55 is illustrated in FIG. 5 (which shows only the tetrahedral atoms) down the direction of the straight 10-membered ring channels. There is a single unit cell unit in FIG. 5 Error! Reference source not found., whose limits are defined by the box. Table VI lists the typical positions of each tetrahedral atom in the unit cell in units of Ångströms. Each tetrahedral atom is bonded to bridging atoms, which are also bonded to adjacent tetrahedral atoms. Tetrahedral atoms are those capable of having tetrahedral coordination, including one or more of, but not limiting, lithium, beryllium, boron, magnesium, aluminum, silicon, phosphorous, titanium, chromium, manganese, iron, cobalt, nickel, copper, zinc, zirconium, gallium, germanium, arsenic, indium, tin, and antimony. Bridging atoms are those capable of connecting two tetrahedral atoms, examples which include, but not limiting, oxygen, nitrogen, fluorine, sulfur, selenium, and carbon atoms.

TABLE VI

Positions of tetrahedral (T) atoms for the ITQ-55 structure. Values, in units of Ångströms, are approximate and are typical when T = silicon and the bridging atoms are oxygen.

| Atoms | x (Å) | y (Å) | z (Å) |
|---|---|---|---|
| T01 | 12.759 | 8.224 | 8.934 |
| T02 | 14.059 | 11.794 | 0.998 |
| T03 | 11.771 | 10.088 | 13.568 |
| T04 | 12.623 | 11.812 | 5.674 |
| T05 | 16.530 | 11.780 | 2.714 |
| T06 | 15.245 | 8.218 | 7.129 |
| T07 | 13.401 | 8.226 | 11.857 |
| T08 | 15.507 | 10.720 | 5.364 |
| T09 | 11.679 | 11.813 | 2.804 |
| T10 | 1.566 | 1.554 | 8.934 |
| T11 | 2.866 | 5.124 | 0.998 |
| T12 | 0.577 | 3.418 | 13.568 |
| T13 | 1.430 | 5.141 | 5.674 |
| T14 | 5.337 | 5.109 | 2.714 |
| T15 | 4.051 | 1.548 | 7.129 |
| T16 | 2.208 | 1.556 | 11.857 |
| T17 | 4.314 | 4.050 | 5.364 |
| T18 | 0.486 | 5.143 | 2.804 |
| T19 | 8.980 | 8.224 | 5.550 |
| T20 | 7.680 | 11.794 | 13.487 |
| T21 | 9.968 | 10.088 | 0.917 |
| T22 | 9.116 | 11.812 | 8.811 |
| T23 | 5.209 | 11.780 | 11.770 |
| T24 | 6.495 | 8.218 | 7.355 |
| T25 | 8.338 | 8.226 | 2.627 |
| T26 | 6.232 | 10.720 | 9.121 |
| T27 | 10.060 | 11.813 | 11.680 |
| T28 | 20.173 | 1.554 | 5.550 |
| T29 | 18.873 | 5.124 | 13.487 |
| T30 | 21.162 | 3.418 | 0.917 |
| T31 | 20.309 | 5.141 | 8.811 |
| T32 | 16.403 | 5.109 | 11.770 |
| T33 | 17.688 | 1.548 | 7.355 |
| T34 | 19.532 | 1.556 | 2.627 |
| T35 | 17.426 | 4.050 | 9.121 |
| T36 | 21.253 | 5.143 | 11.680 |
| T37 | 8.980 | 5.116 | 5.550 |
| T38 | 7.680 | 1.546 | 13.487 |
| T39 | 9.968 | 3.252 | 0.917 |
| T40 | 9.116 | 1.529 | 8.811 |
| T41 | 5.209 | 1.561 | 11.770 |

TABLE VI-continued

Positions of tetrahedral (T) atoms for the ITQ-55 structure.
Values, in units of Ångströms, are approximate and are typical
when T = silicon and the bridging atoms are oxygen.

| Atoms | x (Å) | y (Å) | z (Å) |
|---|---|---|---|
| T42 | 6.495 | 5.123 | 7.355 |
| T43 | 8.338 | 5.115 | 2.627 |
| T44 | 6.232 | 2.620 | 9.121 |
| T45 | 10.060 | 1.527 | 11.680 |
| T46 | 20.173 | 11.786 | 5.550 |
| T47 | 18.873 | 8.216 | 13.487 |
| T48 | 21.162 | 9.923 | 0.917 |
| T49 | 20.309 | 8.199 | 8.811 |
| T50 | 16.403 | 8.231 | 11.770 |
| T51 | 17.688 | 11.793 | 7.355 |
| T52 | 19.532 | 11.785 | 2.627 |
| T53 | 17.426 | 9.290 | 9.121 |
| T54 | 21.253 | 8.198 | 11.680 |
| T55 | 12.759 | 5.116 | 8.934 |
| T56 | 14.059 | 1.546 | 0.998 |
| T57 | 11.771 | 3.252 | 13.568 |
| T58 | 12.623 | 1.529 | 5.674 |
| T59 | 16.530 | 1.561 | 2.714 |
| T60 | 15.245 | 5.123 | 7.129 |
| T61 | 13.401 | 5.115 | 11.857 |
| T62 | 15.507 | 2.620 | 5.364 |
| T63 | 11.679 | 1.527 | 2.804 |
| T64 | 1.566 | 11.786 | 8.934 |
| T65 | 2.866 | 8.216 | 0.998 |
| T66 | 0.577 | 9.923 | 13.568 |
| T67 | 1.430 | 8.199 | 5.674 |
| T68 | 5.337 | 8.231 | 2.714 |
| T69 | 4.051 | 11.793 | 7.129 |
| T70 | 2.208 | 11.785 | 11.857 |
| T71 | 4.314 | 9.290 | 5.364 |
| T72 | 0.486 | 8.198 | 2.804 |
| T73 | 10.870 | 9.915 | 7.242 |
| T74 | 22.063 | 3.244 | 7.242 |
| T75 | 10.870 | 3.426 | 7.242 |
| T76 | 22.063 | 10.096 | 7.242 |

In the case of oxygen, it is also possible that the bridging oxygen is also connected to a hydrogen atom to form a hydroxyl group (—OH—). In the case of carbon, it is also possible that the carbon is also connected to two hydrogen atoms to form a methylene group (—CH$_2$—). For example, bridging methylene groups are present in the zirconium diphosphonate, MIL-57. See: C. Serre, G. Férey, *J. Mater. Chem.* 12, p. 2367 (2002). In the case of nitrogen, it is also possible that the nitrogen bridging atom is part of an imidazolate anion. For example, bridging imidazolate groups are present in the zinc(II) imidazolate zeolite-type compounds, Zn(mim)$_2$.2H$_2$O, Zn(eim)$_2$.H$_2$O, and Zn(eim/mim)$_2$.1.25H$_2$O. See: X-C. Huang, Y-Y. Lin, J-P. Zhang, X-M. Chen, *Angew. Chem. Int. Ed.* 45, p. 1557-1559 (2006). Bridging sulfur and selenium atoms have been seen in the UCR-20-23 family of microporous materials. See: N. Zheng, X. Bu, B. Wang, P. Feng, *Science* 298, p. 2366 (2002). Bridging fluorine atoms have been seen in lithium hydrazinium fluoroberyllate, which has the ABW structure type. See: M. R. Anderson, I. D. Brown, S. Vilminot, *Acta Cryst.* B29, p. 2626 (1973). Since tetrahedral atoms may move about due to other crystal forces (presence of inorganic or organic species, for example), or by the choice of tetrahedral and bridging atoms, a range of ±1.0 Ångström is implied for the x and coordinate positions and a range of ±0.5 Ångström for the y and z coordinate positions.

The complete structure of ITQ-55 is built by connecting multiple unit cells as defined above in a fully-connected three-dimensional framework. The tetrahedral atoms in one unit cell are connected to certain tetrahedral atoms in all of its adjacent unit cells. While Table V lists the connections of all the tetrahedral atoms for a given unit cell of ITQ-55, the connections may not be to the particular atom in the same unit cell but to an adjacent unit cell. All of the connections listed in Table V are such that they are to the closest tetrahedral (T) atoms, regardless of whether they are in the same unit cell or in adjacent unit cells.

Although the Cartesian coordinates given in Table VI may accurately reflect the positions of tetrahedral atoms in an idealized structure, the true structure can be more accurately described by the connectivity between the framework atoms as shown in Table V above.

Another way to describe this connectivity is by the use of coordination sequences as applied to microporous frameworks by W. M. Meier and H. J. Moeck, in the *Journal of Solid State Chemistry* 27, p. 349 (1979). In a microporous framework, each tetrahedral atom, $N_0$, (T-atom) is connected to $N_1$=4 neighboring T-atoms through bridging atoms (typically oxygen). These neighboring T-atoms are then connected to $N_2$ T-atoms in the next shell. The $N_2$ atoms in the second shell are connected to $N_3$ T-atoms in the third shell, and so on. Each T-atom is only counted once, such that, for example, if a T-atom is in a 4-membered ring, at the fourth shell the $N_1$ atom is not counted second time, and so on. Using this methodology, a coordination sequence can be determined for each unique T-atom of a 4-connected net of T-atoms. The following line lists the maximum number of T-atoms for each shell.

$N_0=1$ $N_1 \leq 4$ $N_2 \leq 12$ $N_3 \leq 36$ $N_k \leq 4 \cdot 3^{k-1}$

TABLE VII

Coordination sequence for ITQ-55 structure

| Atom | coordination sequence | | | | | | | | | |
|---|---|---|---|---|---|---|---|---|---|---|
| T1 | 4 | 10 | 20 | 36 | 54 | 73 | 100 | 135 | 181 | 224 |
| T2 | 4 | 9 | 17 | 30 | 53 | 81 | 102 | 123 | 161 | 209 |
| T3 | 4 | 10 | 20 | 34 | 52 | 76 | 104 | 133 | 165 | 203 |
| T4 | 4 | 11 | 21 | 32 | 49 | 76 | 108 | 141 | 173 | 210 |
| T5 | 4 | 12 | 22 | 34 | 46 | 74 | 108 | 144 | 174 | 212 |
| T6 | 4 | 10 | 18 | 32 | 56 | 82 | 103 | 128 | 170 | 217 |
| T7 | 4 | 10 | 20 | 34 | 54 | 81 | 106 | 134 | 176 | 222 |
| T8 | 4 | 10 | 21 | 36 | 54 | 74 | 98 | 131 | 172 | 217 |
| T9 | 4 | 11 | 19 | 33 | 57 | 79 | 103 | 136 | 172 | 217 |
| T10 | 4 | 9 | 17 | 31 | 51 | 75 | 104 | 133 | 165 | 206 |

One way to determine the coordination sequence for a given structure is from the atomic coordinates of the framework atoms using the computer program zeoTsites (see G. Sastre, J. D. Gale, *Microporous and mesoporous Materials* 43, p. 27 (2001).

The coordination sequence for the ITQ-55 structure is given in Table VII. The T-atom connectivity as listed in Table V and is for T-atoms only. Bridging atoms, such as oxygen usually connects the T-atoms. Although most of the T-atoms are connected to other T-atoms through bridging atoms, it is recognized that in a particular crystal of a material having a framework structure, it is possible that a number of T-atoms may not connected to one another. Reasons for non-connectivity include, but are not limited by T-atoms located at the edges of the crystals and by defects sites caused by, for example, vacancies in the crystal. The framework listed in Table V and Table VII is not limited in any way by its composition, unit cell dimensions or space group symmetry.

While the idealized structure contains only 4-coordinate T-atoms, it is possible under certain conditions that some of the framework atoms may be 5- or 6-coordinate. This may occur, for example, under conditions of hydration when the composition of the material contains mainly phosphorous and aluminum T-atoms. When this occurs it is found that T-atoms may be also coordinated to one or two oxygen atoms of water molecules (—OH$_2$), or of hydroxyl groups (—OH). For example, the molecular sieve AlPO$_4$-34 is known to reversibly change the coordination of some aluminum T-atoms from 4-coordinate to 5- and 6-coordinate upon hydration as described by A. Tuel et al. in *J. Phys. Chem. B* 104, p. 5697 (2000). It is also possible that some framework T-atoms can be coordinated to fluoride atoms (—F) when materials are prepared in the presence of fluorine to make materials with 5-coordinate T-atoms as described by H. Koller in *J. Am. Chem Soc.* 121, p. 3368 (1999).

In second place this invention refers to a method to synthesize the microporous crystalline material ITQ-55

According to this invention, the method to synthesize the microporous crystalline material, ITQ-55, may include a reaction mixture that includes at least: one or several sources of SiO$_2$, one or several sources of organic cation R, at least one source of anions selected among hydroxide anions, fluoride anions and combinations of the same and water, it undergoes heating at a temperature between 80 and 200° C., and because the reaction mixture has a composition, in terms of molar ratios, between the intervals $R^+/SiO_2$=0.01-1.0,
$OH^-/SiO_2$=0-3.0
$F^-/SiO_2$=0-3.0
$(F^-+OH^-)/SiO_2$=0.01-3.0,
$H_2O/SiO_2$=1-50.

According to an additional particular embodiment of the method the reaction mixture may include, also, one or more source of GeO$_2$ and because it has a composition, in terms of molar ratios, included between the intervals $GeO_2/SiO_2$=0 and 0.5
$R^+/(SiO_2+GeO_2)$=0.01-1.0,
$F^-/(SiO_2+GeO_2)$=0.0-3.0,
$OH^-/(SiO_2+GeO_2)$=0.0-3.0,
$(F^-+OH^-)/(SiO_2+GeO_2)$=0.01-3.0
$H_2O/(SiO_2+GeO_2)$=1-50.

According to one additional particular embodiment of the method, the anion is preferably fluoride and the reaction mixture has a composition, in terms of molar ratios, between the intervals $GeO_2/SiO_2$=0 and 0.5
$R^+/(SiO_2+GeO_2)$=0.01-1.0,
$F^-/(SiO_2+GeO_2)$=0.01-3.0,
$H_2O/(SiO_2+GeO_2)$=1-50.

According to another additional particular embodiment of the method, the anion is preferably hydroxide and may have a reaction mixture that has a composition, in terms of molar ratios, between the intervals $GeO_2/SiO_2$=0 and 0.5
$R^+/(SiO_2+GeO_2)$=0.01-1.0,
$OH^-/(SiO_2+GeO_2)$=0.01-3.0,
$H_2O/(SiO_2+GeO_2)$=1-50.

According to one additional particular embodiment of the method, the reaction mixture can include, also, at least, one source of one or more trivalent elements X.

In one particular embodiment, the reaction mixture comprises exclusively: one or several sources of SiO$_2$, at least one source of one or several trivalent elements X, one or several sources of organic cation R, at least one source of anions selected among hydroxide anions, fluoride anions and the combinations of the same, and water, and it has a composition, in terms of molar ratios, between the intervals $R^+/SiO_2$=0.01-1.0,
$X_2O_3/SiO_2$=0-0.1, excluding the value 0.
$OH^-/SiO_2$=0-3.0
$F^-/SiO_2$=0-3.0
$(OH^-+F^-)/SiO_2$=0.0-3.0, excluding the value 0, and
$H_2O/SiO_2$=1-50.

According to this embodiment, if you add to the reaction mixture, at least one source of GeO$_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$OH^-/(SiO_2+GeO_2)$=0-3.0
$F^-/(SiO_2+GeO_2)$=0-3.0
$(OH^-+F^-)/(SiO_2+GeO_2)$=0.0-3.0, excluding the value 0, and
$H_2O/(SiO_2+GeO_2)$=1-50.

According to another particular embodiment the reaction mixture comprises exclusively: one or several sources of SiO$_2$, at least one source of one or several trivalent elements X, one or several sources of organic cation R, one or several sources of hydroxide anions, and water, and it has a composition, in terms of molar ratios, between the intervals $R^+/SiO_2$=0.01-1.0,
$X_2O_3/SiO_2$=0-0.1, excluding the value 0,
$OH^-/SiO_2$=0-3.0, excluding the value 0, and
$H_2O/SiO_2$=1-50.

According to this embodiment, if you add to a reaction mixture, at least one source of GeO$_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$OH^-/(SiO_2+GeO_2)$=0-3.0, excluding the value 0, and
$H_2O/(SiO_2+GeO_2)$=1-50.

According to a particular embodiment the reaction mixture comprises exclusively: one or several sources of SiO$_2$,
at least one source of one or several trivalent elements X
one or several sources of organic cation R,
one or several sources of fluoride anions, and
water,
and has a composition, in terms of molar ratios, between the intervals $R^+/SiO_2$=0.01-1.0,
$X_2O_3/SiO_2$=0-0.1, excluding the value 0,
$F^-/SiO_2$=0-3.0, excluding the value 0, and
$H_2O/SiO_2$=1-50.

According to this embodiment, if to reaction mixture you add, at least one source of GeO$_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$F^-/(SiO_2+GeO_2)$=0-3.0, excluding the value 0, and
$H_2O/(SiO_2+GeO_2)$=1-50.

According to another preferred embodiment, in the method previously described, the reaction mixture may also include, at least one source of other tetravalent elements Y, different from Si and Ge.

According to one particular embodiment, the reaction mixture comprises exclusively: one or several sources of SiO$_2$, at least one source of one or several tetravalent elements Y, one or several sources of organic cation R, at least one source of anions selected between hydroxide anions, fluoride anions and combinations of them, and water, and it has a composition, in terms of molar ratios, between the intervals $R^+/SiO_2$=0.01-1.0,
$YO_2/SiO_2$=0-0.1, excluding the value 0,
$OH^-/SiO_2$=0-3.0,
$F^-/SiO_2$=0-3.0
$(OH^-+F^-)/SiO_2$=0-3.0, excluding the value 0, and
$H_2O/SiO_2$=1-50.

According to this embodiment, if to the reaction mixture you add, at least one source of $GeO_2$, the composition, in terms of molar ratios will be between the intervals
$GeO_2/SiO_2$=0 and 0.5, excluding the value 0
$R^+/(SiO_2+GeO_2)$=0.01-1.0,
$YO_2/(SiO_2+GeO_2)$=0-0.1, excluding the value 0,
$OH^-/(SiO_2+GeO_2)$=0-3.0,
$F^-/(SiO_2+GeO_2)$=0-3.0
$(OH^-+F^-)/(SiO_2+GeO_2)$=0-3.0, excluding the value 0, and
$H_2O/(SiO_2+GeO_2)$=1-50.

According to another particular embodiment of the method, the reaction mixture comprises exclusively: one or several sources of $SiO_2$, at least a source of one or several tetravalent elements Y one or several sources of organic cation R, one or several sources of hydroxide anions, and water, and it has a composition, in terms of molar ratios, between the intervals
$R^+/SiO_2$=0.01-1.0,
$YO_2/SiO_2$=0-0.1, excluding the value 0,
$OH^-/SiO_2$=0-3.0, excluding the value 0, and
$H_2O/SiO_2$=1-50.

According to this embodiment, if you add to the reaction mixture, at least one source of $GeO_2$, the composition, in terms of molar ratios will be between the intervals
$GeO_2/SiO_2$=0 and 0.5, excluding the value 0
$R^+/(SiO_2+GeO_2)$=0.01-1.0,
$YO_2/(SiO_2+GeO_2)$=0-0.1, excluding the value 0,
$OH^-/(SiO_2+GeO_2)$=0-3.0, excluding the value 0, and
$H_2O/(SiO_2+GeO_2)$=1-50.

According to another particular embodiment of the method, the reaction mixture comprises exclusively: one or several sources of $SiO_2$, at least one source of one or several tetravalent elements Y, one or several sources of organic cation R, one or several sources of fluoride anions, and water, and it has a composition, in terms of molar ratios, between the intervals
$R^+/SiO_2$=0.01-1.0,
$YO_2/SiO_2$=0-0.1, excluding the value 0,
$F^-/SiO_2$=0-3.0, excluding the value 0, and
$H_2O/SiO_2$=1-50.

According to this embodiment, if you add to the reaction mixture, at least one source of $GeO_2$, the composition, in terms of molar ratios will be between the intervals
$GeO_2/SiO_2$=0 and 0.5, excluding the value 0
$R^+/(SiO_2+GeO_2)$=0.01-1.0,
$YO_2/(SiO_2+GeO_2)$=0-0.1, excluding the value 0,
$F^-/(SiO_2+GeO_2)$=0-3.0, excluding the value 0, and
$H_2O/(SiO_2+GeO_2)$=1-50.

According to another particular embodiment of the described method, the reaction mixture may include one or several sources of several trivalent elements X as well as one or several sources of one or several tetravalent elements.

According to one particular embodiment, the reaction mixture comprises exclusively: one or several sources of $SiO_2$, at least one source of one or several trivalent elements X, at least one source of one or several tetravalent elements Y, and/or several sources of organic cation R, at least one source of anions selected among hydroxide anions, fluoride anions and combinations of the same, and water, and the reaction mixture has a composition, in terms of molar ratios, between the intervals
$R^+/SiO_2$=0.01-1.0,
$X_2O_3/SiO_2$=0-0.1, excluding the value 0,
$YO_2/SiO_2$=0-0.1, excluding the value 0,
$OH^-/SiO_2$=0-3.0
$F^-/SiO_2$=0-3.0
$(OH^-+F^-)/SiO_2$=0-3.0, excluding the value 0, and
$H_2O/SiO_2$=1-50

According to this embodiment, if you add to the reaction mixture, at least one source of $GeO_2$, the composition, in terms of molar ratios will be between the intervals
$GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$YO_2/(SiO_2+GeO_2)$=0-0.1, excluding the value 0,
$OH^-/(SiO_2+GeO_2)$=0-3.0
$F^-/(SiO_2+GeO_2)$=0-3.0
$(OH^-+F^-)/(SiO_2+GeO_2)$=0-3.0, excluding the value 0, and
$H_2O/(SiO_2+GeO_2)$=1-50

According to another particular embodiment the reaction mixture comprises exclusively: one or several sources of $SiO_2$, at least one source of one or several trivalent elements X, at least one source of one or several tetravalent elements Y, one or several sources of organic cation R, one or several sources of hydroxide anions, and water, and it has a composition, in terms of molar ratios, between the intervals
$R^+/SiO_2$=0.01-1.0,
$X_2O_3/SiO_2$=0-0.1, excluding the value 0,
$YO_2/SiO_2$=0-0.1, excluding the value 0,
$OH^-/SiO_2$=0-3.0, excluding the value 0, and
$H_2O/SiO_2$=1-50.

According to this embodiment, if you add to the reaction mixture, at least one source of $GeO_2$, the composition, in terms of molar ratios will be between the intervals
$GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$YO_2/(SiO_2+GeO_2)$=0-0.1, excluding the value 0,
$OH^-/(SiO_2+GeO_2)$=0-3.0, excluding the value 0, and
$H_2O/(SiO_2+GeO_2)$=1-50.

According to another particular embodiment the reaction mixture comprises exclusively: one or several sources of $SiO_2$, at least one source of one or several trivalent elements X, at least one source of one or several tetravalent elements Y, one or several sources of organic cation R, one or several sources of fluoride anions, and water, and it has a composition, in terms of molar ratios, between the intervals
$R^+/SiO_2$=0.01-1.0,
$X_2O_3/SiO_2$=0-0.1, excluding the value 0,
$YO_2/SiO_2$=0-0.1, excluding the value 0,
$F^-/SiO_2$=0-3.0 excluding the value 0, and
$H_2O/SiO_2$=1-50

According to this embodiment, if you add to the reaction mixture, at least one source of $GeO_2$, the composition, in terms of molar ratios will be between the intervals
$GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$YO_2/(SiO_2+GeO_2)$=0-0.1, excluding the value 0,
$F^-/(SiO_2+GeO_2)$=0-3.0 excluding the value 0, and
$H_2O/(SiO_2+GeO_2)$=1-50.

According to the method previously described, the reaction mixture can include, also, a source of inorganic cations M of charge +n, selected among H+, at least one inorganic cation of charge +n selected between alkaline, alkaline earth metals and combinations of the same, and a mixture of both.

According to a preferred embodiment of the described method, the cation R can be $N^2,N^2,N^2,N^5,N^5,N^5,3a,6a$-octamethyloctahydropentalene-2,5-diammonium. In a general manner, one may say that the reaction mixture can have a composition, in terms of molar ratios, between the intervals $GeO_2/SiO_2=0$ and 0.5,
$R^+/(SiO_2+GeO_2)=0.01-1.0$,
$M^{+n}/(SiO_2+GeO_2)=0-1.0$
$OH^-/(SiO_2+GeO_2)=0-3.0$
$F^-/(SiO_2+GeO_2)=0-3.0$
$(F^-+OH^-)/(SiO_2+GeO_2)=0-3$,
$X_2O_3/(SiO_2+GeO_2)=0-0.1$,
$YO_2/(SiO_2+GeO_2)=0-0.1$, and
$H_2O/(SiO_2+GeO_2)=1-50$.

According to one particular embodiment, the composition of the reaction mixture that gives rise to obtaining the ITQ-55 material may represent in a general way the following formula with the values of the parameters that are indicated in terms of molar ratios:

$$rR_{1/p}(OH){:}sM_{1/n}OH{:}tX_2O_3{:}uYO_2{:}vF{:}gGeO_2{:}(1-g)SiO_2{:}wH_2O$$

where M is one or several inorganic cations of charge +n; preferably alkaline or alkaline earth, X is one or several trivalent elements, preferably Al, B, Ga, Fe, Cr or mixtures of them; Y is one or several tetravalent elements different from Si, preferably Zr, Ti, Sn, V or mixtures of them; R is one or more organic cations, p is the charge of the cation or the average charge of the cations, preferably $N^2,N^2,N^2,N^5$, $N^5,N^5,3a,6a$-octamethylo-octahydropentalene-2,5-diammonium; F is one or more sources of fluoride ions, preferably HF, $NH_4F$, or a mixture of both, and the values of g, r, s, t, u, v and w vary in the intervals:

g=0-0.5, preferably 0-0.33
r=ROH/$SiO_2$=0.01-1.0, preferably 0.1-1.0
s=$M_{1/n}$OH/$SiO_2$=0-1.0, preferably 0-0.2
t=$X_2O_3$/$SiO_2$=0-0.1, preferably 0-0.05
u=$YO_2$/$SiO_2$=0-0.1, preferably 0-0.05
v=F/$SiO_2$=0-3.0, preferably 0-2.0
w=$H_2O$/$SiO_2$=1-50, preferably 1-20

The components of the synthesis mixture may come from different sources, and depending on these, the times and crystallization conditions may vary.

Preferably the thermal treatment of the mixture is carried out at a temperature between 110 and 200° C. The thermal treatment of the reaction mixture can be carried out as static or with stirring of the mixture. Once the crystallization is concluded the solid product is separated by filtration or centrifuging and dried. The subsequent calcining at temperatures greater than 350° C., preferably between 400 and 1300° C., and more preferably between 600 and 1000° C., produces the decomposition of the organic remnants occluded within the zeolite and their expulsion, leaving the zeolitic channels clear.

The source of $SiO_2$ may be, for example, tetraethylorthosilicate, colloidal silica, amorphous silica and mixtures thereof The fluoride anion may be used as mobilizing agent of the precursor species. The source of fluoride ions is preferably HF, $NH_4F$ or a mixture of both.

The organic cation(s), represented by R, are added to the reaction mixture preferably in hydroxide form, of another salt, for example, a halide, and a hydroxide mixture and another salt, that is to say additionally, a source may be added of alkaline, alkaline earth ions, or mixtures of both (M), in hydroxide form or in salt form.

In a preferred way the organic cation R is $N^2,N^2,N^2,N^5$, $N^5,N^5,3a,6a$-octamethyl-octahydropentalene-2,5-diammonium, and it is added preferably in a form selected between hydroxide, another salt and a hydroxide mixture and another salt, preferably a halide.

The organic cation $N^2,N^2,N^2,N^5,N^5,N^5,3a,6a$-octamethylo-octahydropentalene-2,5-diammonium is synthesized following the process represented in the following outline:

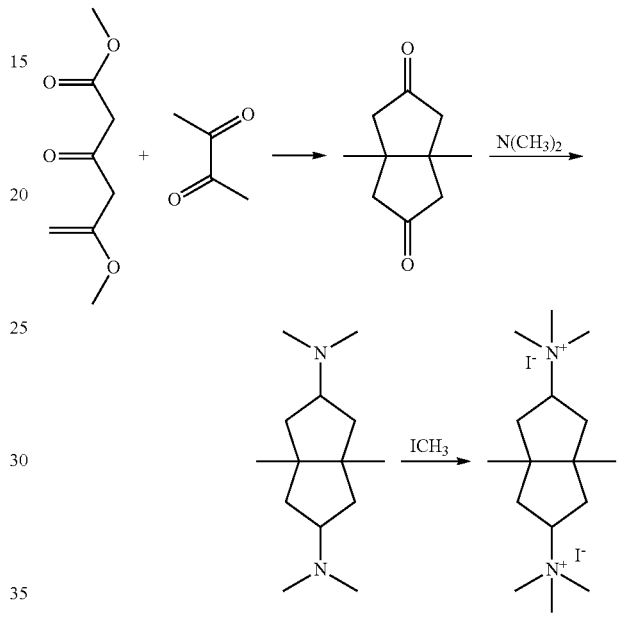

In this process a aldolic condensation reaction is carried out followed by a decarboxylation reaction between the dimethyl 1,3-acetonadicarboxylate with 2,3-butanodione to give rise to the corresponding diketone, 3a,6a-dimethyltetrahydropentalene-2,5(1H,3H)-dione. The diketone is transformed into the corresponding diamine by means of a reductive amination reaction in the presence of dimethylamine and using sodium cyanoborohydride as reducer, giving rise to the diamine, $N^2,N^2,N^5,N^5,3a,6a$-hexamethyloctahydropentalene-2,5-diamine. This diamine is subsequently quaternized with methyl iodide to give rise to the salt of $N^2,N^2,N^2,N^5,N^5,N^5,3a,6a$-octamethyloctahydropentalene-2,5-diammonium di-iodide.

The salt of dialkylammonium diodide may be dissolved in water and exchanged with its hydroxide form using an anionic exchange resin in hydroxide form.

According to one particular embodiment of the method, a quantity is added to the reaction mixture of microporous crystalline material, ITQ-55, from this invention as promoter of the crystallization in a quantity between 0.01 and 20% by weight, preferably between 0.05 and 10% by weight with regard to the total of added inorganic oxides.

Also, the material produced by means of this invention may be pelletized in accordance with well-known techniques.

This invention also refers to the use of the microporous crystalline material previously described and obtained according to the process previously described.

The material of this invention, may be used as a catalyst or component of catalysts in transformation processes of organic compounds, or as adsorbent in adsorption and separation processes of organic compounds.

For its use in the previously mentioned processes it is preferable that ITQ-55 is in its calcined form without organic matter in its interior.

The ITQ-55 material used in these catalytic applications may be in its acidic form and/or exchanged with appropriate cations, such as $H^+$ and/or an inorganic cation of charge +n, selected among alkaline, alkaline-earth metals, lanthanides and combinations thereof.

The ITQ-55 material used in adsorption/separation processes may be in its purely siliceous form, that is to say, not containing elements other than silicon and oxygen in its composition.

The ITQ-55 material used in adsorption/separation processes may be in silica-germania form, that is to say, not containing elements other than silicon, germanium and oxygen in its composition.

The ITQ-55 material is particularly appropriate for use as selective adsorbent of $CO_2$ in the presence of hydrocarbons, preferably methane, ethane, ethylene and combinations of the same, in streams that contain these gases, well as adsorbent in powdered or pelletized form or in membrane form.

According to one specific embodiment, the ITQ-55 material may be used for the separation of $CO_2$ and methane.

According to one specific embodiment, the ITQ-55 material may be used for the separation of $CO_2$ and ethane.

According to one specific embodiment, the ITQ-55 material may be used for the separation of $CO_2$ and ethylene.

According to another particular embodiment, the ITQ-55 material is particularly appropriate for the separation in adsorption processes of hydrocarbons of 1 or 2 carbon atoms that contain these gases, as well as adsorbent in powdered or pelletized form or in membrane form.

According to one specific embodiment, the ITQ-55 material is used as a selective adsorbent of ethylene in the presence of ethane.

According to another specific embodiment, the ITQ-55 material is used as selective adsorbent of ethylene in the presence of methane.

Throughout the description and the claims the word "includes" and its variants does not seek to exclude other technical characteristics, additives, components or steps. For the experts in the matter, other objects, advantages and characteristic of the invention shall come partly from the description and partly from the practice of the invention.

This invention is illustrated by means of the following examples that do not seek to be restrictive thereof.

EXAMPLES

Example 1

Preparation of the $N^2,N^2,N^2,N^5,N^5,N^5$,3a,6a-octamethyloctahydropentalene-2,5-diammonium dihydroxide To a recently prepared and thoroughly mixed solution of 5.6 g $NaHCO_3$ in 360.0 mL of $H_2O$ (pH=8) is added 48.2 mL (526.3 mmol) of dimethyl 1,3-acetonedicarboxylate followed by 23.0 mL (263.2 mmol) of 2,3-butanodione. The mixture remains under continuous stirring for 72 hr. After this period the abundant precipitate obtained is filtered under vacuum and cooled in a bath of ice, being acidified to pH=5 with HCl (5%). The raw precipitate is extracted three times with $CHCl_3$, washing the set of organic phases with brine and drying them on MgSO4. The mixture is filtered through folded filter and the filtrate obtained concentrated under vacuum and used in the following stage without additional purification.

The resultant solid is suspended in a mixture of 300.00 mL of HCl (1M) and 30.0 mL of glacial acetic acid and thereafter heated under reflux for 24 hr. The resulting mixture is cooled first to room temperature and then in an ice bath, extracting thereafter five time with $CH_2Cl_2$, drying the set of organic phases over $MgSO_4$. The rough precipitate obtained is filtered through folded filter and concentrated under vacuum obtaining 32.7 g (75%) of the desired diketone, 3a,6a-dimethyltetrahydropentalene-2,5 (1H,3H)-dione.

This diketone is transformed into the corresponding diamine by means of the method that is described below. 350.0 mL of a solution 1.0 M of dimethylamine in methanol is cooled in an ice bath and onto it is dripped a solution of HCl 5 N in MeOH until obtaining pH=7-8. Then 16.7 g is added (100.7 mmol) of the previously prepared diketone dissolved in the minimum possible quantity of MeOH, followed by 10.2 g (161.2 mmol) of $NaBH_3CN$. The temperature is allowed to rise to room temperature and remains under continuous stirring for 72 hr.

The possible excess of $NaBH_3CN$ is neutralized by adding HCl 5 N in MeOH until reaching pH=2, displacing the HCN formed with a stream of $N_2$ until a saturated solution in KOH. The mixture is partially concentrated under vacuum and the rough resultant is basified with a solution of KOH (25%) until reaching pH=12 and it is saturated with NaCl. The rough resultant obtained is extracted three times with $CH_2Cl_2$, drying the set of organic phases on $MgSO_4$. It is concentrated under vacuum obtaining 21.4 g (95%) of the desired diamine, $N^2,N^2,N^5,N^5$,3a,6a hexamethyloctahydropentalene-2,5-diamine.

Subsequently, the diamine is transformed into the quaternary diammonium ketone. For that, 21.6 g of the previously obtained diamine is dissolved in 100.0 mL of MeOH and to it is added slowly, by means of a compensated pressure funnel, 45.0 mL (722.8 mmol) of $CH_3I$ diluted in 40.0 mL of MeOH. Almost immediately a yellowish precipitate appears. The mixture remains under continuous stirring for 72 hr and then 45.0 ml is added (722.8 mmol) of $CH_3I$ remaining under continuous stirring until completing one week. The precipitate obtained is filtered under vacuum washing with abundant diethyl ether, providing 37.1 g of the quaternary ammonium salt desired in iodide form, $N^2,N^2,N^2,N^5,N^5,N^5$,3a,6a-octamethyloctahydropentalene-2,5-diammonium diiodide.

The filtrate is concentrated under vacuum and the viscous solid obtained is washed with abundant acetone, a new precipitate appears that after filtering and drying under vacuum provides another 2.0 g of the ammonium salt (80%).

The iodide of the cation is exchanged by hydroxide using an ionic exchange resin in accordance with the following method: 20 g (44 mmol) of iodide of the cation ($RI_2$) is dissolved in water. To the solution obtained is added 89 g of Dowex SBR resin and it remains under stirring until the following day. Subsequently, it is filtered, it is washed with distilled water and a solution of $N^2,N^2,N^2,N^5,N^5,N^5$,3a,6a dihydroxide is obtained—octamethyloctahydropentalene-2,5-diammonium (R(OH)2) that is titrated with HCl (aq.), using phenolphthalein as indicator, an efficiency being obtained in the exchange greater than 92%.

The final solution contains 0.47 equivalent of hydroxide per 1000 g of solution.

Example 2

Zeolite Preparation ITQ-55

6 g is added of an aqueous solution of colloidal silica at 40% (Ludox ACE-40) to 42.5 g of a solution of $N^2,N^2,N^2,N^5,N^5,N^5$,3a,6a-octamethyloctahydropentalene 2,5-diammonium dihydroxide—(R(OH)$_2$) that contains 0.47 equivalent of hydroxide in 1000 g. The mixture is left evaporating under stirring until complete elimination of the surplus water until reaching the final composition that is indicated. Finally, a solution of 0.74 g of ammonium fluoride is added in 2.5 g of water. The composition of the gel is:

$SiO_2$: 0.25 R(OH)$_2$: 0.5 NH$_4$F: 5 H$_2$O.

The mixture obtained is introduced in an autoclave provided with an internal sleeve of polytetrafluoroethylene and is warmed at 150° C. over 10 days in an electrical furnace provided with a rotation system. The X-ray diffractogram of the solid obtained on filtering, washing with distilled water and drying at 100° C. is shown in FIG. 1 and presents the listing of the most characteristic peaks that appears in the Table III. The calcining at 800° C. in air for 3 hours allows eliminating the occluded organic species. The X-ray diffraction pattern of the calcined zeolite ITQ-55 is shown in FIG. 2 and presents the most characteristic peaks that appears in Table IV and indicates that the material is stable during this process.

Example 3

Zeolite Preparation ITQ-55

8 g of tetraethylorthosilicate (TEOS) is added to 40.8 g of a solution of $N^2,N^2,N^2,N^5,N^5,N^5$,3a,6a-octamethyloctahydropentalene-2,5-diammonium dihydroxide (R(OH)2) that contains 0.47 equivalent of hydroxide in 1000 g. The mixture is left evaporating under stirring until complete elimination of the ethanol coming from the hydrolysis of the TEOS plus the quantity of water necessary until reaching the final composition that is indicated. Finally, 0.77 g of a solution of hydrofluoric acid is added (50% of HF by weight). The composition of the gel is:

$SiO_2$: 0.25 R(OH)$_2$: 0.5 HF: 5 H$_2$O.

The mixture obtained is introduced into a autoclave provided with an internal sleeve of polytetrafluoroethylene and is warmed at 15 over 10 days in an electrical furnace provided with a rotation system. The solid obtained on filtering, washing with distilled water and drying at 100° C. is ITQ-55.

Example 4

Zeolite Preparation ITQ-55

6 g is added from a aqueous solution of colloidal silica at 40% (Ludox ACE-40) 42.5 g of a solution of $N^2,N^2,N^2,N^5,N^5,N^5$,3a,6a-octamethyloctahydropentalene-2,5-diammonium (R(OH)2) dihydroxide that contains 0.47 equivalent of hydroxide in 1000 g. Thereafter 0.14 g of aluminum hydroxide is added (57% Al$_2$O$_3$) and the mixture is left evaporating under stirring until complete elimination of the surplus water until reaching the final composition that is indicated. Finally, a solution of 0.74 g of ammonium fluoride is added in 2.5 g of water. The composition of the gel is:

$SiO_2$: 0.02 Al$_2$O$_3$: 0.25 R(OH)2: 0.5 NH$_4$F: 5 H$_2$O.

Figure 3:
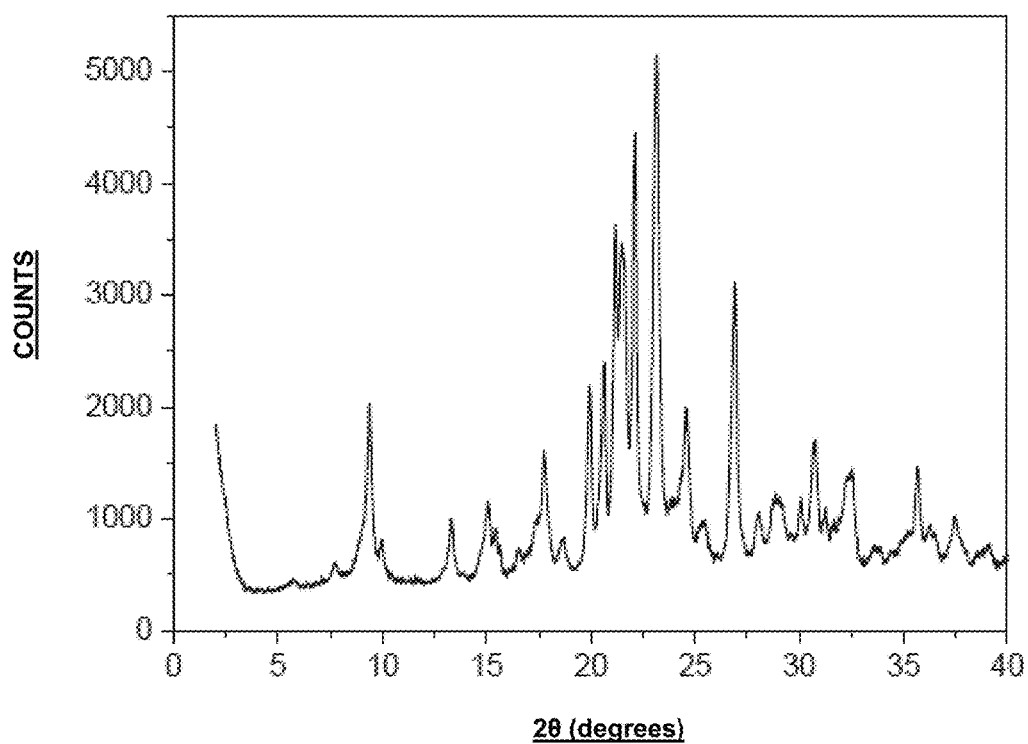
FIG. 3 represents the X-ray diffraction pattern of the most characteristic peaks of the ITQ-55 material that contains Al and Si in its composition, as is synthesized, obtained according to example 4.

The mixture obtained is introduced in an autoclave provided of an internal sleeve of polytetrafluoroethylene and is warmed at 150° C. over 14 days in an electrical furnace provided with a rotation system. The solid obtained on filtering, washing with distilled water and drying at 100° C. presents the diffractogram of X-rays that is shown in FIG. 3 and indicates that it is zeolite ITQ-55.

Example 5

Zeolite Preparation ITQ-55

To 0.087 g of Ti tetraethoxide (IV) (TEOTi) is added 8 g of tetraethylorthosilicate (TEOS). Next 40.8 g of a solution of $N^2,N^2,N^2,N^5,N^5,N^5$,3a,6a-octamethyloctahydropentalene-2,5-diammonium dihydroxide (R(OH)$_2$) is added that contains 0.47 equivalent of hydroxide in 1000 g. The mixture is left evaporating under stirring until complete elimination of the ethanol coming from the hydrolysis of TEOS and TEOTi plus the quantity of water necessary until reaching the final composition that is indicated. Finally, 0.77 g of a solution of hydrofluoric acid is added (50% of HF by weight). The composition of the gel is:

$SiO_2$: 0.01 TiO$_2$: 0.25 R(OH)$_2$: 0.5 HF: 5 H$_2$O.

The mixture obtained is introduced in a autoclave provided with an internal sleeve of polytetrafluoroethylene and is warmed at 150° C. over 14 days in an electrical furnace provided with a rotation system. The solid obtained on filtering, washing with distilled water and drying at 100° C. is ITQ-55.

Example 6

Zeolite Preparation ITQ-55

6 g is added from a aqueous solution of colloidal silica at 40% (Ludox ACE-40) 42.5 g of a solution of $N^2,N^2,N^2,N^5,N^5,N^5$,3a,6a-octamethyloctahydropentalene-2,5-diammonium dihydroxide (R(OH)$_2$) that contains 0.47 equivalent of hydroxide in 1000 g. Next 0.1 g of H$_3$BO$_3$ is added and the mixture is left evaporating under stirring until complete elimination of the surplus water until reaching the final composition that is indicated. Finally, a solution of 0.74 g of ammonium fluoride is added in 2.5 g of water. The composition of the gel is:

$SiO_2$: 0.02 B$_2$O$_3$: 0.25 R(OH) 2: 0.5 NH$_4$F: 5 H$_2$O.

The mixture obtained is introduced into a autoclave provided with an internal sleeve of polytetrafluoroethylene and is warmed at 150° C. over 14 days in an electrical furnace provided with a rotation system. The solid obtained on filtering, washing with distilled water and drying at 100° C. is zeolite ITQ-55.

Example 7

Zeolite Preparation ITQ-55

To 8 g of tetraethylorthosilicate (TEOS) is added 36.6 g of a solution of $N^2,N^2,N^2,N^5,N^5,N^5$,3a,6a-octamethyloctahydropentalene-2,5-diammonium dihydroxide (R(OH)$_2$) that contains 0.53 equivalent of hydroxide in 1000 g. Next 0.0476 g of H$_3$BO$_3$ is added. The mixture is left evaporating under stirring until complete elimination of the ethanol coming from the hydrolysis of the TEOS plus the quantity of water necessary until reaching the final composition that is indicated. The composition of the gel is:

$SiO_2$: 0.01 $B_2O_3$: 0.25 $R(OH)_2$: 10 $H_2O$.

The mixture obtained is introduced in an autoclave provided of an internal sleeve of polytetrafluoroethylene and is warmed to 150° C. over 14 days in an electrical furnace provided with a rotation system. The solid obtained on filtering, washing with distilled water and drying at 100° C. is ITQ-55.

Example 8

Zeolite Preparation ITQ-55

To 8 g of tetraethylorthosilicate (TEOS) is added 36.3 g of a solution of $N^2,N^2,N^2,N^5,N^5,N^5$,3a,6a-octamethyloctahydropentalene-2,5-diammonium dihydroxide $(R(OH)2)$ that contains 0.532 equivalent of hydroxide in 1000 g. Next 0.805 g of $GeO_2$ is added. The mixture is left evaporating under stirring until complete elimination of the ethanol coming from the hydrolysis of the TEOS plus the quantity of water necessary until reaching the final composition that is indicated. The composition of the gel is:

$SiO_2$: 0.2 $GeO_2$: 0.25 $R(OH)_2$: 10 $H_2O$.

The mixture obtained is introduced in a autoclave provided with an internal sleeve of polytetrafluoroethylene and is warmed at 150° C. over 14 days in an electrical furnace provided with a rotation system. The solid obtained on filtering, washing with distilled water and drying at 100° C. is ITQ-55.

Example 9

Adsorption of $CO_2$ at 30° C. In the ITQ-55 Material of Example 2

The measurement of the adsorption capacity of $CO_2$ of the ITQ-55 material, prepared according to the example 2, at 30° C. and 9 bar corresponds to 2.96 mmoles/g. Likewise, the value obtained after carrying out 20 adsorption/desorption cycles is of 2.95 mmoles/g, which demonstrates that the material ITQ-55 conserves its adsorption capacity after a high number of cycles.

Example 10

Adsorption of $CO_2$ at 60° C. In the ITQ-55 Material of Example 2

The measurement of the $CO_2$ adsorption capacity of the ITQ-55 material, prepared according to the example 2, at 60° C. and 9 bar corresponds to 2.35 mmoles/g.

Example 11

Methane Adsorption at 60° C. In the ITQ-55 Material of Example 2

The measurement of the methane adsorption capacity of the ITQ-55 material, prepared according to the example 2, at 60° C. and 9 bar corresponds to 0.22 mmoles/g, after equilibrating for 24 hours at this temperature and pressure.

Example 12

Methane Adsorption at 30° C. In the ITQ-55 Material of Example 2

The measurement of the methane adsorption capacity of the ITQ-55 material, prepared according to the example 2, at 30° C. and 9 bar corresponds to 0.18 mmoles/g after equilibrating for 24 hours at this temperature and pressure. The lowest adsorption capacity under these conditions regarding the one observed in the example 5 indicates the drop in diffusion capacity of the methane through the zeolite ITQ-55 pores.

Example 13

Determination of the Selectivity in the Separation of $CO_2$ and Methane in the ITQ-55 Material of Example 2

Figure 4:
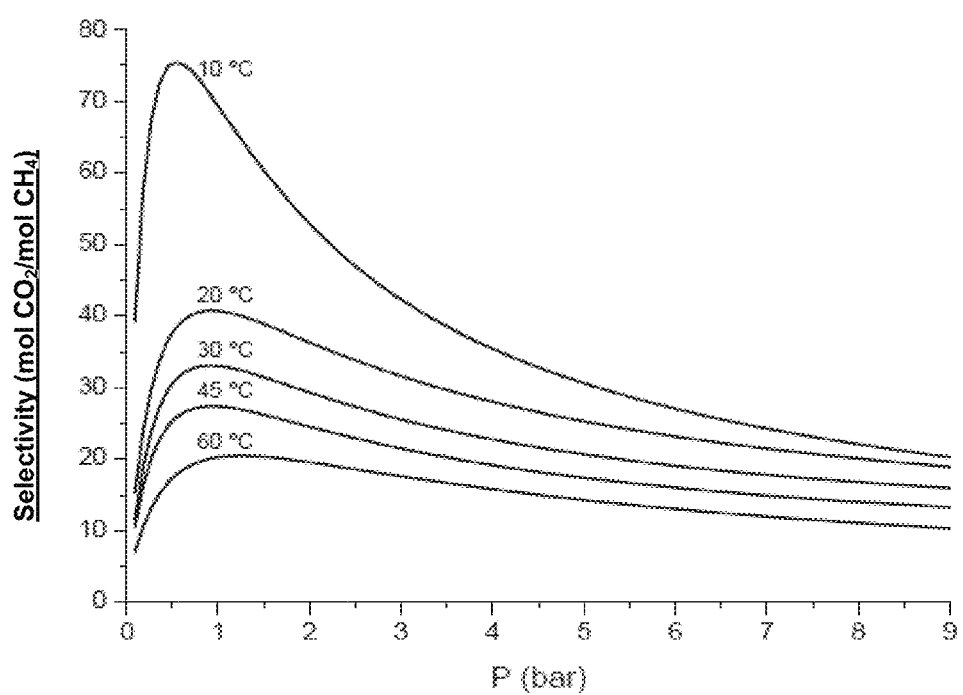
FIG. 4 represents the adsorption selectivity of $CO_2$ over that of methane in the ITQ-55 material in its calcined form, obtained according to example 2. The selectivity is expressed as the ratio of the adsorption capacity obtained starting from the isotherms of the pure gases.

The selectivity in methane and $CO_2$ separation has been considered through the ratio of the adsorption values of the isotherms of the pure gases of $CO_2$ and methane at identical pressure and temperature. It is considered that the selectivity in the separation process will be better insofar as the ratio between these values is greater. In the FIG. 4 the variation of this ratio is shown with the gas pressure at different temperatures.

Example 14

Ethane Adsorption at 30° C. In the ITQ-55 Material of Example 2

The measurement of the adsorption capacity of ethane of the ITQ-55 material, prepared according to the example 2, at 30° C. and 9 bar corresponds to 0.14 mmoles/g after equilibrating for 24 hours at this temperature and pressure.

Example 15

Ethylene Adsorption at 30° C. In the ITQ-55 Material of Example 2

The measurement of the ethylene adsorption capacity of the ITQ-55 material, prepared according to the example 2, at 30° C. and 9 bar corresponds to 0.75 mmoles/g after equilibrating for 24 hours at this temperature and pressure.

Additional Embodiments

Additionally or alternately, the present invention can include one or more of the following embodiments.

Embodiment 1. A microporous crystalline material of zeolitic nature characterized because it has, in calcined state and in absence of defects in its crystalline matrix manifested by the presence of silanols, the empiric formula $$x(M_{1/n}XO_2):yYO_2:gGeO_2:(1-g)SiO_2$$

in which

M is selected between H+, at least one inorganic cation of charge +n, and a mixture of both, X is at least one chemical element of oxidation state +3, Y is at least one chemical element with oxidation state +4 different from Si, x takes a value between 0 and 0.2, both included, y takes a value between 0 and 0.1, both included, g takes a value between 0 and 0.5, both included, and because the material, as synthesized, has an X-ray diffraction pattern with, at least, the angle values 2θ (degrees) and relative intensities ($I/I_0$):

| 2θ (degrees) ± 0.5 | Intensity (I/I₀) |
|---|---|
| 5.8 | w |
| 7.7 | w |
| 8.9 | w | where $I_0$ is the intensity from the most intense pick to which is assigned a value of 100 w is a weak relative intensity between 0 and 20%,
m is an average relative intensity between 20 and 40%,
f is a strong relative intensity between 40 and 60%,
and mf is a very strong relative intensity between 60 and 100%.

Embodiment 2. A microporous crystalline material of zeolitic nature according to embodiment 1, characterized because, in calcined state, it has an X-ray diffraction pattern with, at least, the angle values 2θ (degrees) and relative intensities ($I/I_0$):

| 2θ (degrees) ± 0.5 | Intensity (I/I0) |
|---|---|
| 6.2 | w |
| 7.8 | w |
| 8.0 | w |
| 9.8 | mf |
| 10.0 | m |
| 10.3 | w |
| 12.3 | w |
| 13.4 | w |
| 13.7 | w |
| 15.0 | w |
| 15.2 | w |
| 16.8 | w |
| 18.1 | w |
| 20.1 | w |
| 21.3 | w |
| 23.5 | w |
| 23.9 | w |
| 26.8 | w | where
w is a weak relative intensity between 0 and 20%,
m is an medium relative intensity between 20 and 40%,
f is a strong relative intensity between 40 and 60%, and
mf it is a very strong relative intensity between 60 and 100%.

Embodiment 3. A microporous crystalline material of zeolitic nature according to embodiment 1, characterized because X is selected between Al, Ga, B, Fe, Cr and mixtures thereof Embodiment 4. A microporous crystalline material of zeolitic nature according to embodiment 1, characterized because Y is selected between Zr, Ti, Sn, V and mixtures thereof Embodiment 5. A microporous crystalline material of zeolitic nature according to embodiment 1, characterized because M is selected among H+, at least one inorganic cation of charge +n selected between alkaline, alkaline-earth metals and combinations thereof, and a mixture of both.

Embodiment 6. A microporous crystalline material of zeolitic nature according to embodiment 1, characterized because "x" is 0, "y" is 0, and "g" is 0.

Embodiment 7. A microporous crystalline material of zeolitic nature according to embodiment 1, characterized because "x" is 0, "y" is 0 and "g" is different from 0.

Embodiment 8. A microporous crystalline material of zeolitic nature according to embodiment 1, characterized because:

X is Al, Ga, B, Fe, Cr, and combinations of the same,
y takes the value 0, and
g takes the value 0.

Embodiment 9. A microporous crystalline material of zeolitic nature according to embodiment 1, characterized because:
Y is Ti, Zr, Sn and combinations thereof
x takes the value 0, and
g takes the value 0.

Embodiment 10. A microporous crystalline material of zeolitic nature according to embodiment 1, characterized because:
X is Al, Ga, B, Fe, Cr, and combinations thereof,
Y is Ti, Zr, Sn, and combinations thereof and
g takes the value 0.

Embodiment 11. A microporous crystalline material of zeolitic nature according to embodiment 1 or 2, characterized because:
X is Al, Ga, B, Fe, Cr, and combinations thereof,
y takes the value 0, and
g takes a value different from 0 and less than 0.33.

Embodiment 12. A microporous crystalline material of zeolitic nature according to embodiment 1, characterized because:
Y is Ti, Zr, Sn, and combinations thereof,
x takes the value 0, and
g takes a value different from 0 and less than 0.33.

Embodiment 13. A microporous crystalline material of zeolitic nature according to embodiment 1 or 2, characterized because:
X is Al, Ga, B, Fe, Cr, and combinations thereof,
Y is Ti, Zr or Sn, and
g takes a value different from 0 and less than 0.33.

Embodiment 14. A method to synthesize the microporous crystalline material characterized because a reaction mixture that includes at least
one or several sources of $SiO_2$
one or several sources of organic cation R,
at least one source of anions selected among hydroxide anions, fluoride anions and the combinations thereof, and water
heating to a temperature between 80 and 200° C., and the reaction mixture having a composition, in terms of molar ratios, comprised between the intervals
$R^+/SiO_2 = 0.01\text{-}1.0$
$OH^-/SiO_2 = 0\text{-}3.0$
$F^-/SiO_2 = 0\text{-}3.0$
$(F^- + OH^-)/SiO_2 = 0.01\text{-}3.0$,
$H_2O/SiO_2 = 1\text{-}50$.

Embodiment 15. A method according to embodiment 14, characterized because a reaction mixture includes, also, one or more sources of $GeO_2$ and having a composition, in terms of molar ratios, between the intervals
$GeO_2/SiO_2 = 0$ and 0.5
$R^+/(SiO_2 + GeO_2) = 0.01\text{-}1.0$,
$F^-/(SiO_2 + GeO_2) = 0.0\text{-}3.0$,
$OH^-/(SiO_2 + GeO_2) = 0.0\text{-}3.0$,
$(F^- + OH^-)/(SiO_2 + GeO_2) = 0.01\text{-}3.0$
$H_2O/(SiO_2 + GeO_2) = 1\text{-}50$.

Embodiment 16. A method according to the embodiments 14 or 15, characterized because the anion is fluoride and having a composition, in terms of molar ratios, between the intervals
$GeO_2/SiO_2 = 0$ and 0.5
$R^+/(SiO_2 + GeO_2) = 0.01\text{-}1.0$,
$F^-/(SiO_2 + GeO_2) = 0.01\text{-}3.0$,
$H_2O/(SiO_2 + GeO_2) = 1\text{-}50$.

Embodiment 17. A method according to the embodiments 14 or 15, characterized because the anion is hydroxide and having a composition, in terms of molar ratios, between the intervals $GeO_2/SiO_2=0$ and 0.5,
$R^+/(SiO_2+GeO_2)=0.01$-1.0,
$OH^-/(SiO_2+GeO_2)=0.01$-3.0,
$H_2O/(SiO_2+GeO_2)=1$-50.

Embodiment 18. A method according to embodiment 14, characterized because the reaction mixture also includes, at least, one source of one or more trivalent X elements.

Embodiment 19. A method according to embodiment 14, characterized because the reaction mixture also includes, at least one source of other tetravalent elements Y, different from Si and Ge.

Embodiment 20. A method according to embodiment 14, characterized because the source of organic cation R is $N^2,N^2,N^2,N^5,N^5,N^5,3a,6a$-octamethyloctahydropentalene-2,5-diammonium.

Embodiment 21. A method according to embodiment 20, characterized because the organic cation R is added in selected form between hydroxide, another salt and a hydroxide mixture and another salt.

Embodiment 22. A method according to embodiment 14, characterized because a quantity is added to the reaction mixture of the microporous crystalline material as promoter of the crystallization, in a quantity between 0.01 and 20% by weight with regard to the total of inorganic oxides added.

Embodiment 23. A microporous crystalline material of zeolitic nature having a framework of tetrahedral (T) atoms connected by bridging atoms, wherein the tetrahedral atom is defined by connecting the nearest T atoms in the manner described in the following Table:

| ITQ-55 tetrahedral atom interconnections | |
| --- | --- |
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67 |

Embodiment 24. A microporous crystalline material of zeolitic nature according to embodiment 1 or 2 having a framework of tetrahedral (T) atoms connected by bridging atoms, wherein the tetrahedral atom is defined by connecting the nearest T atoms in the manner described in the following Table:

| ITQ-55 tetrahedral atom interconnections | |
| --- | --- |
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |

| ITQ-55 tetrahedral atom interconnections | |
|---|---|
| T atom | Connected to: |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67 |

Embodiment 25. A microporous crystalline material of zeolitic nature according to embodiment 23, wherein the material, as synthesized, has an X-ray diffraction pattern with, at least, the angle values 2θ (degrees) and relative intensities ($I/I_0$):

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where $I_0$ is the intensity from the most intense pick to which is assigned a value of 100 w is a weak relative intensity between 0 and 20%, m is an average relative intensity between 20 and 40%, f is a strong relative intensity between 40 and 60%, and mf is a very strong relative intensity between 60 and 100%.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A microporous crystalline material of zeolitic nature having, in calcined state and in absence of defects in its crystalline matrix manifested by the presence of silanols, the empiric formula $$x(M_{1/n}XO_2):yYO_2:gGeO_2:(1-g)SiO_2$$

in which

M is selected between H$^+$, at least one inorganic cation of charge +n, and a mixture of both, X is at least one chemical element of oxidation state +3, Y is at least one chemical element with oxidation state +4 different from Si, x takes a value between 0 and 0.2, both included, y takes a value between 0 and 0.1, both included, g takes a value between 0 and 0.5, both included, and wherein the material, as synthesized, has an X-ray diffraction pattern with, at least, the angle values 2θ (degrees) and relative intensities ($I/I_0$):

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |

-continued

| 2θ (degrees) ± 0.5 | Intensity (I/I₀) |
|---|---|
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where $I_0$ is the intensity from the most intense peak to which is assigned a value of 100 w is a weak relative intensity between 0 and 20%, m is an average relative intensity between 20 and 40%, f is a strong relative intensity between 40 and 60%, and mf is a very strong relative intensity between 60 and 100%.

2. A microporous crystalline material of zeolitic nature according to claim 1, wherein X is selected from the group consisting of Al, Ga, B, Fe, Cr and mixtures thereof.

3. A microporous crystalline material of zeolitic nature according to claim 1, wherein Y is selected from the group consisting of Zr, Ti, Sn, V and mixtures thereof.

4. A microporous crystalline material of zeolitic nature according to claim 1, wherein M is selected among H⁺, at least one inorganic cation of charge +n selected from the group consisting of alkaline, alkaline-earth metals and combinations thereof.

5. A microporous crystalline material of zeolitic nature according to claim 1, wherein "x" is 0, "y" is 0, and "g" is 0.

6. A microporous crystalline material of zeolitic nature according to claim 1, wherein "x" is 0, "y" is 0 and "g" is different from 0.

7. A microporous crystalline material of zeolitic nature according to claim 1, wherein:
X is selected from the group consisting of Al, Ga, B, Fe, Cr, and combinations of the same,
y takes the value 0, and
g takes the value 0.

8. A microporous crystalline material of zeolitic nature according to claim 1, wherein:
Y is selected from the group consisting of Ti, Zr, Sn and combinations thereof
x takes the value 0, and
g takes the value 0.

9. A microporous crystalline material of zeolitic nature according to claim 1, wherein:
X is selected from the group consisting of Al, Ga, B, Fe, Cr, and combinations thereof,
Y is selected from the group consisting of Ti, Zr, Sn, and combinations thereof and
g takes the value 0.

10. A microporous crystalline material of zeolitic nature according to claim 1, wherein:
Y is selected from the group consisting of Ti, Zr, Sn, and combinations thereof,
x takes the value 0, and
g takes a value different from 0 and less than 0.33.

11. A microporous crystalline material of zeolitic nature according to claim 1, wherein, in calcined state, it has an X-ray diffraction pattern with, at least, the angle values 2θ (degrees) and relative intensities (I/I₀):

| 2θ (degrees) ± 0.5 | Intensity (I/I0) |
|---|---|
| 6.2 | w |
| 7.8 | w |
| 8.0 | w |
| 9.8 | mf |
| 10.0 | m |
| 10.3 | w |
| 12.3 | w |
| 13.4 | w |
| 13.7 | w |
| 15.0 | w |
| 15.2 | w |
| 16.8 | w |
| 18.1 | w |
| 20.1 | w |
| 21.3 | w |
| 23.5 | w |
| 23.9 | w |
| 26.8 | w | where w is a weak relative intensity between 0 and 20%, m is an medium relative intensity between 20 and 40%, f is a strong relative intensity between 40 and 60%, and mf it is a very strong relative intensity between 60 and 100%.

12. A microporous crystalline material of zeolitic nature according to claim 1 or 11, wherein:
X is selected from the group consisting of Al, Ga, B, Fe, Cr, and combinations thereof,
y takes the value 0, and
g takes a value different from 0 and less than 0.33.

13. A microporous crystalline material of zeolitic nature according to claim 1 or 11, wherein:
X is selected from the group consisting of Al, Ga, B, Fe, Cr, and combinations thereof,
Y is selected from the group consisting of Ti, Zr Sn, and combinations thereof
g takes a value different from 0 and less than 0.33.

14. A microporous crystalline material of zeolitic nature according to claim 1 or 11 having a framework of tetrahedral (T) atoms connected by bridging atoms, wherein the tetrahedral atom is defined by connecting the nearest T atoms in the manner described in the following Table:

| ITQ-55 tetrahedral atom interconnections | |
|---|---|
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |

-continued

| ITQ-55 tetrahedral atom interconnections | |
|---|---|
| T atom | Connected to: |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67. |

15. A method to synthesize the microporous crystalline material of claim 1 by forming a reaction mixture comprising:
one or several sources of $SiO_2$
one or several sources of organic cation R,
at least one source of anions selected from the group consisting of hydroxide anions, fluoride anions and the combinations thereof, and water
heating to a temperature between 80 and 200° C., and the reaction mixture having a composition, in terms of molar ratios, comprised between the intervals
$R^+/SiO_2$=0.01-1.0
$OH^-/SiO_2$=0-3.0
$F^-/SiO_2$=0-3.0
$(F^-+OH^-)/SiO_2$=0.01-3.0,
$H_2O/SiO_2$=1-50.

16. A method according to claim 15, wherein the reaction mixture also includes, at least, one source of one or more trivalent X elements.

17. A method according to claim 15, wherein the reaction mixture also includes, at least one source of other tetravalent elements Y, different from Si and Ge.

18. A method according to claim 15, wherein the source of organic cation R is $N^2,N^2,N^2,N^5,N^5,N^5$,3a,6a-octamethyloctahydropentalene-2,5-diammonium.

19. A method according to claim 18, wherein the organic cation R is added in selected form the group consisting of hydroxide, another salt and a hydroxide mixture and another salt.

20. A method according to claim 15, wherein a quantity is added to the reaction mixture of the microporous crystalline material as promoter of the crystallization, in a quantity between 0.01 and 20% by weight with regard to the total of inorganic oxides added.

21. A method according to claim 15, wherein the reaction mixture includes one or more sources of $GeO_2$ and having a composition, in terms of molar ratios, between the intervals
$GeO_2/SiO_2$=0 and 0.5
$R^+/(SiO_2+GeO_2)$=0.01-1.0,
$F^-/(SiO_2+GeO_2)$=0.0-3.0,
$OH^-/(SiO_2+GeO_2)$=0.0-3.0,
$(F^-+OH^-)/(SiO_2+GeO_2)$=0.01-3.0
$H_2O/(SiO_2+GeO_2)$=1-50.

22. A method according to the claim 15 or 21, wherein the anion is fluoride and having a composition, in terms of molar ratios, between the intervals
$GeO_2/SiO_2$=0 and 0.5
$R^+/(SiO_2+GeO_2)$=0.01-1.0,
$F^-/(SiO_2+GeO_2)$=0.01-3.0,
$H_2O/(SiO_2+GeO_2)$=1-50.

23. A method according to the claim 15 or 21, wherein the anion is hydroxide and having a composition, in terms of molar ratios, between the intervals
$GeO_2/SiO_2$=0 and 0.5,
$R^+/(SiO_2+GeO_2)$=0.01-1.0,
$OH^-/(SiO_2+GeO_2)$=0.01-3.0,
$H_2O/(SiO_2+GeO_2)$=1-50.

24. A microporous crystalline material of zeolitic nature having a framework of tetrahedral (T) atoms connected by bridging atoms, wherein the tetrahedral atom is defined by connecting the nearest T atoms in the manner described in the following Table:

| ITQ-55 tetrahedral atom interconnections | |
|---|---|
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |

| ITQ-55 tetrahedral atom interconnections | |
|---|---|
| T atom | Connected to: |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67. |

25. A microporous crystalline material of zeolitic nature according to claim 24, wherein the material, as synthesized, has an X-ray diffraction pattern with, at least, the angle values 2θ (degrees) and relative intensities ($I/I_0$):

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where $I_0$ is the intensity from the most intense peak to which is assigned a value of 100 w is a weak relative intensity between 0 and 20%, m is an average relative intensity between 20 and 40%, f is a strong relative intensity between 40 and 60%, and mf is a very strong relative intensity between 60 and 100%.

* * * * *